(12) United States Patent
Parramon et al.

(10) Patent No.: US 7,428,438 B2
(45) Date of Patent: Sep. 23, 2008

(54) SYSTEMS AND METHODS FOR PROVIDING POWER TO A BATTERY IN AN IMPLANTABLE STIMULATOR

(75) Inventors: Jordi Parramon, Valencia, CA (US); Goran N. Marnfeldt, Hollviken (SE); Rafael Carbunaru, Studio City, CA (US); Robert D. Ozawa, Woodland Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 622 days.

(21) Appl. No.: 11/043,642

(22) Filed: Jan. 25, 2005

(65) Prior Publication Data

US 2005/0131495 A1 Jun. 16, 2005

Related U.S. Application Data

(63) Continuation-in-part of application No. 10/609,449, filed on Jun. 27, 2003.

(60) Provisional application No. 60/392,475, filed on Jun. 28, 2002.

(51) Int. Cl.
*A61N 1/00* (2006.01)
(52) U.S. Cl. .......................... 607/61; 607/33
(58) Field of Classification Search ............. 607/30–31, 607/60–61, 32–33
See application file for complete search history.

(56) References Cited

U.S. PATENT DOCUMENTS 4,134,408 A * 1/1979 Brownlee et al. ............. 607/33

5,193,539 A 3/1993 Schulman et al.

(Continued)

FOREIGN PATENT DOCUMENTS

WO WO-97/18857 A1 5/1997

(Continued)

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

(Continued)

*Primary Examiner*—Angela Sykes
*Assistant Examiner*—Joseph Stoklosa
(74) *Attorney, Agent, or Firm*—Wong, Cabello, Lutsch, Rutherford & Brucculeri, LLP

(57) ABSTRACT

An exemplary system for providing power to a rechargeable battery in an implantable stimulator includes a first coil configured to emit a first magnetic field, a coil in the stimulator configured to receive the first magnetic field, and a zero volt recovery (ZVR) circuit in the stimulator configured to use the first magnetic field to cause the coil in the stimulator to be tuned to a frequency of a second magnetic field. The second magnetic field is used to provide the power to recharge the battery. An exemplary method of providing power to recharge a battery in an implantable stimulator includes transmitting a first magnetic field used to provide the power to recharge the battery, transmitting a second magnetic field; and using the second magnetic field to cause a coil in the stimulator to be tuned to a frequency of the first magnetic field.

38 Claims, 21 Drawing Sheets

U.S. PATENT DOCUMENTS

| | | | |
|---|---|---|---|
| 5,193,540 | A | 3/1993 | Schulman et al. |
| 5,312,439 | A | 5/1994 | Loeb |
| 5,405,367 | A | 4/1995 | Schulman et al. |
| 5,642,030 | A * | 6/1997 | Seelye .................. 320/101 |
| 5,750,926 | A | 5/1998 | Schulman et al. |
| 5,769,877 | A * | 6/1998 | Barreras, Sr. ............. 607/61 |
| 5,861,019 | A * | 1/1999 | Sun et al. ................ 607/60 |
| 6,051,017 | A | 4/2000 | Loeb et al. |
| 6,058,330 | A * | 5/2000 | Borza ..................... 607/61 |
| 6,061,596 | A | 5/2000 | Richmond et al. |
| 6,073,050 | A * | 6/2000 | Griffith .................. 607/57 |
| 6,148,235 | A * | 11/2000 | Kuiper ................... 607/29 |
| 6,164,284 | A | 12/2000 | Schulman et al. |
| 6,175,764 | B1 | 1/2001 | Loeb et al. |
| 6,181,965 | B1 | 1/2001 | Loeb et al. |
| 6,185,452 | B1 | 2/2001 | Schulman et al. |
| 6,185,455 | B1 | 2/2001 | Loeb et al. |
| 6,208,894 | B1 | 3/2001 | Schulman et al. |
| 6,212,430 | B1 * | 4/2001 | Kung ..................... 607/61 |
| 6,214,032 | B1 | 4/2001 | Loeb et al. |
| 6,259,937 | B1 | 7/2001 | Schulman et al. |
| 6,315,721 | B2 | 11/2001 | Schulman et al. |
| 6,366,817 | B1 * | 4/2002 | Kung ..................... 607/61 |
| 6,400,991 | B1 * | 6/2002 | Kung ..................... 607/61 |
| 6,553,263 | B1 | 4/2003 | Meadows et al. |
| 6,567,703 | B1 | 5/2003 | Thompson et al. |
| 6,631,296 | B1 | 10/2003 | Parramon et al. |
| 2002/0055779 | A1 * | 5/2002 | Andrews ................ 623/11.11 |
| 2003/0078634 | A1 * | 4/2003 | Schulman et al. ........... 607/61 |

FOREIGN PATENT DOCUMENTS

| | | |
|---|---|---|
| WO | WO-00/01320 A2 | 1/2000 |
| WO | WO-00/01320 A3 | 1/2000 |
| WO | WO-01/82398 A1 | 11/2004 |

OTHER PUBLICATIONS

Loeb, et al., ANorth Sea: Transducers and Electrodes—Injectable Microstimulator for Functional Electrical Stimulation@, Med. & Biol. Eng. & Computer, North Sea Special Feature, 29 (Nov. 1991), pp. NS13-NS19.

Loeb, et al., ABIONTM Bionic Neurons for Functional and Therapeutic Electrical Stimulation@, 20th Annual International Conference of IEEE Engineering in Medicine and Biology ABiomedical Engineering Towards the Year 2000 and Beyond@, Oct. 29-Nov. 1, 1998, Hong Kong, 5 pages.

* cited by examiner

| MODE | M1 | M2 | M3 | M4 | M5 | M6 |
|---|---|---|---|---|---|---|
| CHARGING | OFF | ON | ON | OFF | OFF | OFF |
| STEP-UP | ON | OFF | OFF | SWITCH | OFF | OFF |
| FSK RX | OFF | ON | ON | OFF | ON | ON |
| OOK RX | OFF | ON | ON | OFF | OFF | OFF |
| TRANSMITTING | ON | OFF | ON | SWITCH | OFF | OFF |

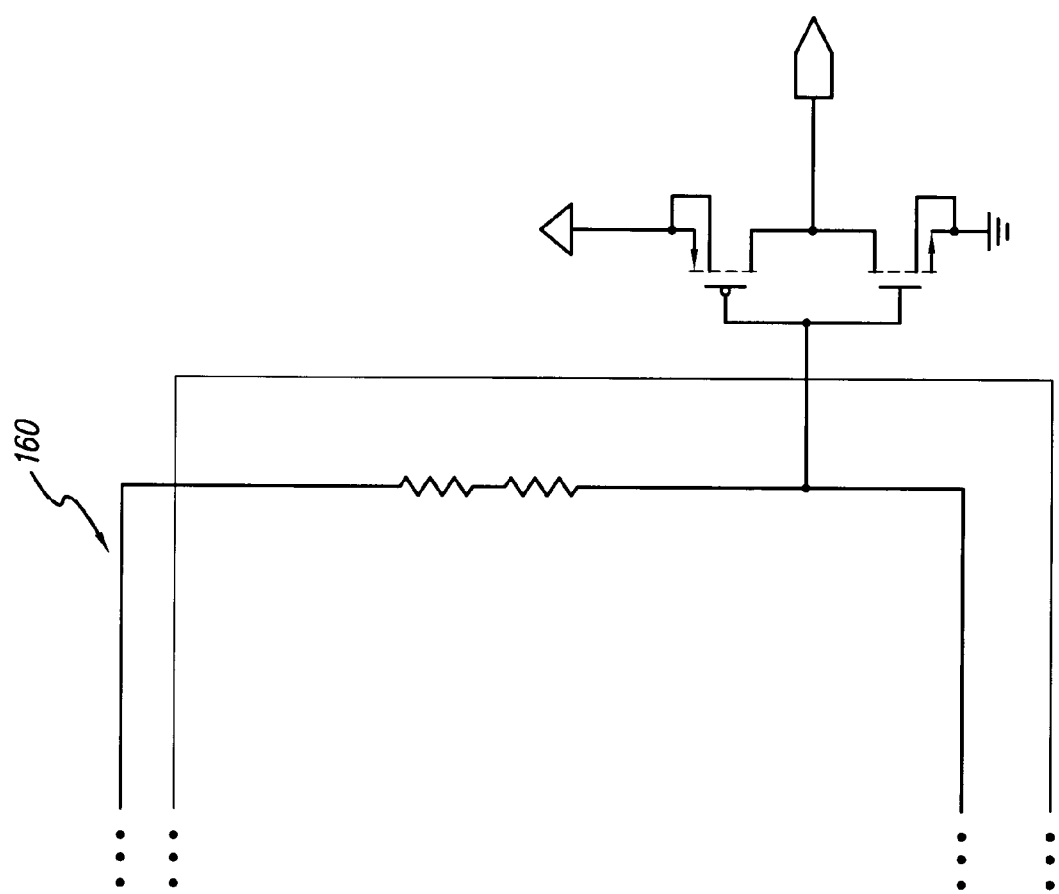

SYSTEMS AND METHODS FOR PROVIDING POWER TO A BATTERY IN AN IMPLANTABLE STIMULATOR

RELATED APPLICATIONS

The present application is a continuation-in-part and claims the priority under 35 U.S.C. § 120 of previous U.S. patent application Ser. No. 10/609,449, filed Jun. 27, 2003, and which is incorporated herein by reference in its entirety. U.S. patent application Ser. No. 10/609,449 claims the benefit under 35 U.S.C. § 119(e) of Provisional Application Ser. No. 60/392,475, filed Jun. 28, 2002, which is also incorporated herein by reference in its entirety.

BACKGROUND

Radio-frequency (RF) powered implantable stimulators and battery powered implantable stimulators are described in the art. See, for instance, U.S. Pat. Nos. 5,193,539 ("Implantable Microstimulator); U.S. Pat. No. 5,193,540 ("Structure and Method of Manufacture of an Implantable Microstimulator"); U.S. Pat. No. 5,312,439 ("Implantable Device Having an Electrolytic Storage Electrode"); U.S. Pat. No. 6,185,452 ("Battery-Powered Patient Implantable Device"); 6,164,284 and 6,208,894 (both titled "System of Implantable Device for Monitoring and/or Affecting Body Parameters"). Each of these patents is incorporated herein by reference in its respective entirety.

Implantable stimulators configured to prevent or treat various disorders associated with prolonged inactivity, confinement or immobilization of one or more muscles are taught, e.g., in U.S. Pat. Nos. 6,061,596 ("Method for Conditioning Pelvis Musculature Using an Implanted Microstimulator"); U.S. Pat. No. 6,051,017 ("Implantable Microstimulator and Systems Employing the Same"); 6,175,764 ("Implantable Microstimulator System for Producing Repeatable Patterns of Electrical Stimulation"); 6,181,965 ("Implantable Microstimulator System for Prevention of Disorders"); 6,185,455 ("Methods of Reducing the Incidence of Medical Complications Using Implantable Microstimulators"); and 6,214,032 ("System for Implanting a Microstimulator"). Each of these patents is incorporated herein by reference in its respective entirety.

A typical implantable stimulator is intended to permanently remain in the body of a patient once it is implanted. Hence, transcutaneous communication between an implantable stimulator and an external device may be important for the stimulator to function properly. For example, communication with the implantable stimulator may be effected to perform a number of functions including, but not limited to, transferring power to the stimulator, transferring data to and from the stimulator, programming the stimulator, and monitoring the stimulator's various functions.

SUMMARY

An exemplary system for providing power to a rechargeable battery in an implantable stimulator includes a first coil configured to emit a first magnetic field, a coil in the stimulator configured to receive the first magnetic field, and a zero volt recovery (ZVR) circuit in the stimulator configured to use the first magnetic field to cause the coil in the stimulator to be tuned to a frequency of a second magnetic field. The second magnetic field is used to provide the power to recharge the battery.

An exemplary method of providing power to recharge a battery in an implantable stimulator includes transmitting a first magnetic field used to provide the power to recharge the battery, transmitting a second magnetic field, and using the second magnetic field to cause a coil in the stimulator to be tuned to a frequency of the first magnetic field.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

FIG. 5 is a table that lists the states of transistor switches M1-M6 for a number of modes of operation of the stimulator according to principles described herein.

Throughout the drawings, identical reference numbers designate similar, but not necessarily identical, elements.

DETAILED DESCRIPTION

Systems and methods for providing power to a battery in an implantable stimulator are described herein. A first coil in an external device may be configured to emit a first magnetic field. A coil in the stimulator is configured to receive the first magnetic field. A zero volt recovery (ZVR) circuit in the stimulator is configured to use the first magnetic field to cause the coil in the stimulator to be tuned to a frequency of a second magnetic field. The second magnetic field is then used to provide power to the battery.

In the following description, for purposes of explanation, numerous specific details are set forth in order to provide a thorough understanding of the present system and method. It will be apparent, however, to one skilled in the art that the present system and method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
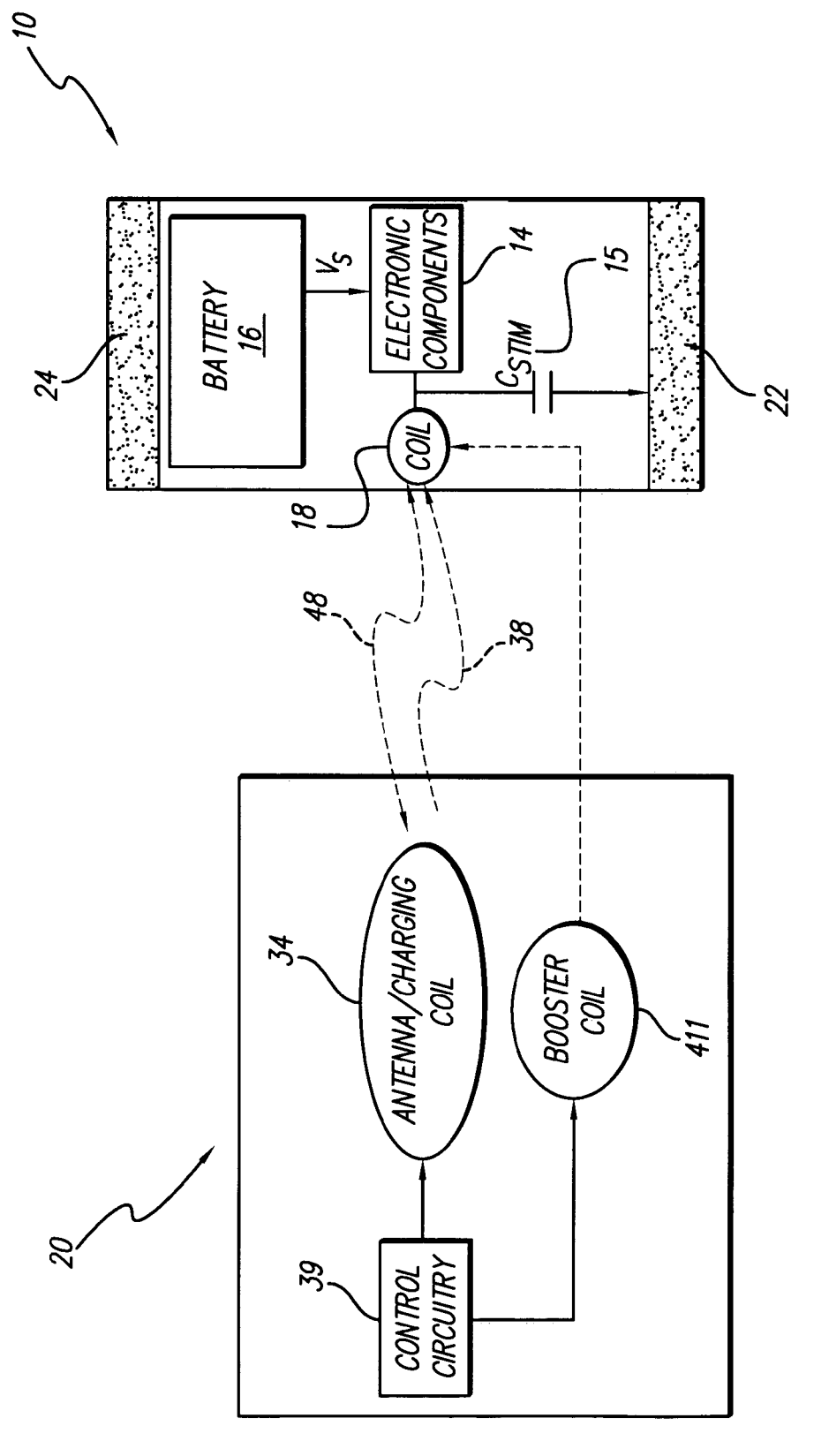
FIG. 1 shows an exemplary implantable stimulator and an exemplary external device according to principles described herein.

FIG. 1 shows an exemplary implantable stimulator (10) and an exemplary external device (20). The implantable stimulator (10) may be any type of implantable medical device, for example, an implantable micro stimulator. Micro stimulators are smaller than conventionally sized stimulators and are more easily implanted in a patient. Micro stimulators may be injected through a large bore needle or placed via a small incision in the skin. An exemplary, but not exclusive, implantable micro stimulator is the BION® micro stimulator (Advanced Bionics® Corporation, Valencia, Calif.) which may be configured to stimulate tissue to alleviate urinary incontinence, reduce pain, or otherwise provide therapy for various disorders. Other examples of implantable stimulators include, but are not limited to, spinal cord stimulators (SCS), cochlear implants, and deep brain stimulators. As used herein and in the appended claims, unless otherwise specifically denoted, the terms "stimulator" and "microstimulator" will be used interchangeably to refer to any implantable medical device that may be implanted within a patient for therapeutic purposes. A typical stimulator or micro stimulator is configured to transcutaneously communicate with an external device.

The implantable stimulator (10) may be implanted in the target tissue area of a patient and the external device (20) may be used to communicate with and/or transfer power to the stimulator (10). Such communication and/or power transfer may include, but is not limited to, transcutaneously transmitting data to the stimulator (10), receiving data from the stimulator (10), transferring power to a battery (16) in the stimulator (10), and/or providing recovery power to the battery (16) when the battery is in a zero volt state. As used herein and in the appended claims, unless otherwise specifically denoted, the term "zero volt state" will be used to refer to a state wherein the battery (16) has been depleted to a voltage level substantially equal to zero volts.

As illustrated in FIG. 1, the implantable stimulator (10) may include a number of components. A battery (16), which may be rechargeable, is configured to output a voltage $V_S$ used to supply the various components within the stimulator (10) with power. A coil (18) is configured to receive and/or emit a magnetic field that is used to communicate with or receive power from the external device (20). A stimulating capacitor (15) and two or more electrodes (22, 24) are configured to stimulate tissue with electric current. One or more of these components may be housed within a case (not shown). The stimulator (10) may include an additional electronic sub-assembly (14) configured to perform a variety of functions as best serves a particular application.

The exemplary external device (20) of FIG. 1 may include control circuitry (39) and an antenna/charging coil (34) configured to emit and/or receive a magnetic field that is used to communicate with the implantable stimulator (10). In some examples, the antenna/charging coil (34) and the coil (18) of the stimulator (10) communicate by sending RF signals across a bidirectional telemetry link (48). The RF signals sent across the bidirectional telemetry link (48) may be modulated using frequency shift keying (FSK) or by some other modulation scheme. The antenna/charging coil (34) and the coil (18) of the stimulator (10) may also communicate via a forward telemetry link (38). The forward telemetry link (38) may use an on/off keying (OOK) modulation scheme. The forward telemetry link (38) is also known as an OOK telemetry link. On/off keying (OOK) modulation is frequency independent and is also known as pulse width modulation (PWM).

The exemplary external device (20) may also include a booster coil (411) configured to emit a magnetic field that is used to provide recovery power to the rechargeable battery (16) when the battery (16) is in a zero volt state. In other words, the booster coil (411) provides a magnetic field that is used in zero volt recovery (ZVR) for the rechargeable battery (16). The magnetic field emitted by the booster coil (411) is also known as a boost field. In some examples, as shown in FIG. 1, the booster coil (411) may provide the boost field to the rechargeable battery (16) via a second forward telemetry link (28). The booster coil (411) and the antenna/charging coil (34) of FIG. 1 are shown as two separate coils for illustrative purposes only. It will be recognized, however, that the functions performed by the booster coil (411) and the antenna/charging coil (34) may be performed by a single coil. For example, the antenna/charging coil (34) may be configured to emit a first magnetic field for communicating with and/or providing power to the stimulator (10) and a second magnetic field used in ZVR. Zero volt recovery will be described in more detail below.

The external device (20) may be configured to perform any number of functions via the bidirectional telemetry link (48), the forward telemetry link (38), and/or the second forward telemetry link (28). As mentioned, the external device (20) may provide ZVR for the rechargeable battery (16). The external device (20) may also be configured to transcutaneously charge the rechargeable battery (16) in the implanted stimulator (10) via the bidirectional telemetry link (48), transcutaneously transmit data to the stimulator (10), and/or receive data from the stimulator (10). The transmitted data may include configuration bits, programming bits, calibration bits, and/or other types of data.

The functions performed by the external device (20) will vary as best serves the particular application of the stimulator (10). The shape and design of the external device (20) will likewise vary. For example, the external device (20) may comprise a chair pad and a base station. In use, the chair pad may be placed on a chair and a patient who has an implanted stimulator (10) may sit on the chair pad to recharge the battery (16) in the stimulator (10) and/or to transfer data between the base station and the stimulator (10). Alternatively, the external device (20) may be housed within a casing that is worn by the patient near the surface of the skin. In general, the external device (20) may be any device configured to communicate with and/or transfer power to an implantable stimulator (10).

Figure 2:
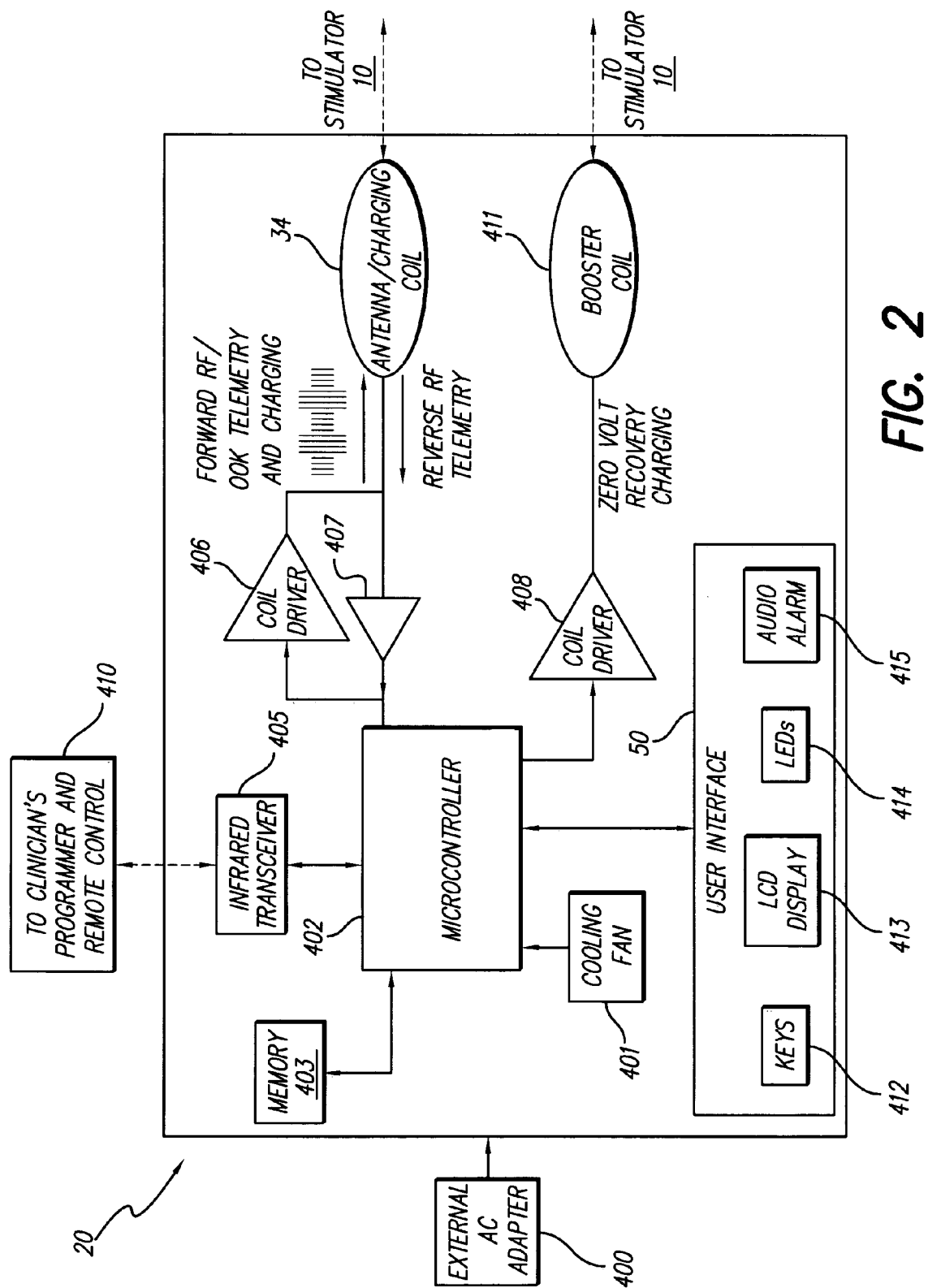
FIG. 2 is a functional block diagram of an exemplary external device according to principles described herein.

FIG. 2 is a functional block diagram of the exemplary external device (20) according to one embodiment. As shown in FIG. 2, the external device (20) may include a number of components, some or all of which are configured to facilitate the transfer of power and/or data to the implantable stimulator (10). For example, the illustrated external device (20) may include memory (403), the antenna/charging coil (34), the booster coil (411), one or more coil driver circuits (406, 408), a user interface (50), and a microcontroller (402). The microcontroller (402) is configured to control the operation of the various components included in the external device (20). A cooling fan (401) may be included to cool the microcontroller (402). The external device (20) may be powered, for example, by an external alternating current (AC) adapter (400). Alternatively, the external device (20) may be powered by a battery or by some other power source.

As shown in FIG. 2, the user interface (50) may include user input keys (412), one or more LCD displays (413), one or more LED displays (414) and/or an audio alarm (415). These controls may assist a user in controlling the external device (20) and/or the stimulator (10). The audio alarm (415) may be used to indicate to the user when the external device (20) has finished charging the stimulator's battery (16; FIG. 1), for example. The audio alarm (415) may also be used as a signal indicator for any other system event or mode.

The external device (20) may further include a receiver (407) configured to receive reverse telemetry signals from the implantable stimulator (10). The receiver (407) may be an amplifier or any other component configured to receive telemetry signals. These signals may then be processed by the microcontroller (402). Furthermore, the microcontroller (402) may communicate with an external clinician programmer and/or a remote control (410) via an infrared transceiver (405) or any other type of signaling.

Figure 3:
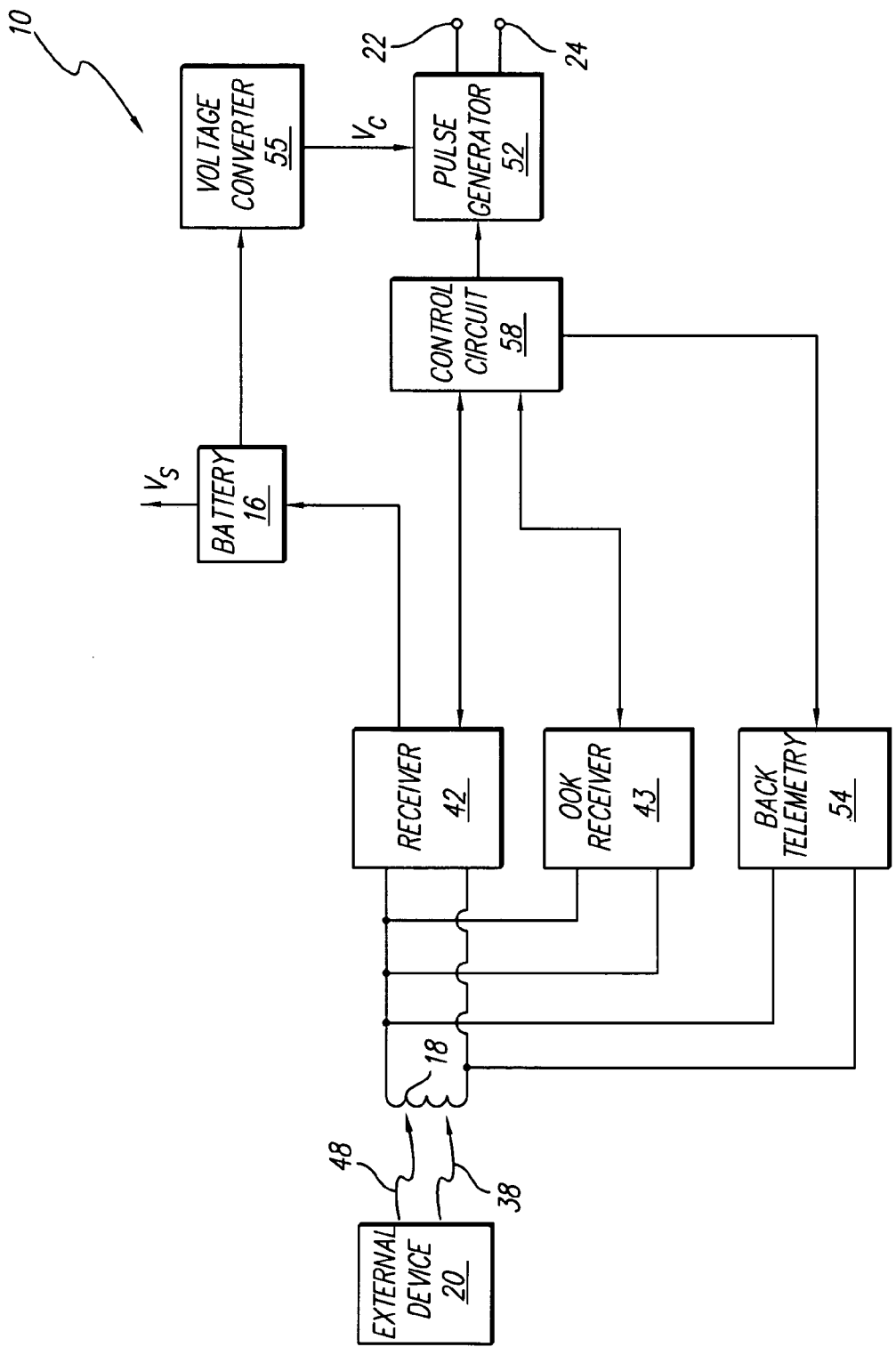
FIG. 3 shows a functional block diagram of an exemplary implantable stimulator according to principles described herein.

FIG. 3 shows a functional block diagram of an exemplary implantable stimulator (10). As shown in FIG. 3, the coil (18) may be coupled to a receiver (42) and configured to receive an RF signal via the bidirectional telemetry link (48). The receiver (42) may be any circuit configured to receive and process an RF signal. For example, the receiver (42) may be a microprocessor, digital signal processor (DSP), application specific integrated circuit (ASIC), processor with firmware, field programmable gate array (FPGA), or any other combination of hardware and/or software.

The RF signal may be sent by the external device (20), for example, and may include a carrier signal having modulated control data. The receiver (42) may then rectify the carrier signal to provide charging power for the rechargeable battery (16) and demodulate the carrier signal to extract the control data. As used herein and in the appended claims, the terms "control data" or "control bits" will be used to refer to any data or bits that are transmitted from the external device (20) to the implantable stimulator (10) or from the implantable stimulator (10) to the external device (20).

As shown in FIG. 3, the control data received by the receiver (42) may be input into a control circuit (58). The control circuit (58) is configured to control the operation of the stimulator (10). For example, the control circuit (58) may cause a pulse generator circuit (52) to generate and deliver electrical stimulation pulses to a patient through the electrodes (22, 24). The control circuit (58) may be a microprocessor, DSP, ASIC, processor with firmware, FPGA, or any other combination of hardware and/or software.

As mentioned, the battery (16) outputs a voltage $V_S$ that is used to supply power to various components of the stimulator (10). The voltage $V_S$ may be a low value such as two to three volts. Hence, the implantable stimulator (10) may also include a voltage converter circuit (55) configured to boost, or step up, the source voltage $V_S$ from its relatively low value to a higher level $V_C$ as needed by the pulse generator circuit (52). The voltage converter circuit (55) may be any combination of electronic components configured to step up a voltage.

In some embodiments, the coil (18) may also be connected to a back telemetry circuit (54) to allow telemetry data to be sent from the stimulator (10) to the external device (20). The back telemetry circuit (54) may be any circuit configured to transmit data.

The coil (18) may also be connected to an OOK receiver (43) to receive OOK modulated data. The OOK receiver (43) may be any circuit configured to receive and process an RF signal that has been OOK modulated. For example, the OOK receiver (43) may be a microprocessor, DSP, ASIC, processor with firmware, FPGA, or any other combination of hardware and/or software. Furthermore, the OOK receiver (43) may be integrated into the receiver (42). The OOK telemetry link (38) allows the external device (20) to communicate with the stimulator (10) even when the stimulator (10) is not actively listening for an RF signal to be transmitted via the bidirectional telemetry link (48), e.g., when the stimulator (10) is operating in a hibernation state or in a storage state. The OOK telemetry link (38) also provides a communication interface between the external device (20) and the stimulator (10) that may be used in emergency situations, e.g., when the bidirectional telemetry link (48) fails or when there is an emergency power shutdown.

Thus, as seen in FIG. 3, the implantable stimulator (10) may be configured to operate in a number of different modes. For example, the stimulator (10) may be configured to operate in a charging mode wherein the incoming RF signal is rectified to provide charging power for the rechargeable battery (16). The stimulator (10) may also operate in a step-up mode wherein the voltage $V_S$ output by the battery (16) is stepped up to a higher value by using pulse width modulation (PWM), on-off switching, or some other method. The stimulator (10) may also operate in an FSK receiving (FSK RX) mode wherein the incoming RF signal is processed by the receiver (42) to extract control data. The stimulator (10) may also operate in an OOK receiving (OOK RX) mode wherein the incoming RF signal is processed by the OOK receiver (43) to extract control data. The stimulator (10) may also operate in a transmitting mode wherein the stimulator (10) transmits data to the external device (20) or to any other component via the back telemetry circuit (54). The stimulator (10) may alternatively operate in a zero volt recovery (ZVR) mode wherein recovery power is provided to the battery (16) if the battery (16) is in a zero volt state. The stimulator (10) may also operate in any other mode not specifically mentioned herein. In some embodiments, the stimulator (10) may operate in two or more modes simultaneously.

A combination of one or more analog and/or digital components may be used to cause the stimulator (10) to operate in one or more of the above mentioned modes. These components will be described in more detail below. Furthermore, the coil (18) may be multiplexed to allow the stimulator (10) to operate in one or more modes. In other words, the same coil (18) may be used in any of the modes of operation. A single multiplexed coil, such as the coil (18) shown in FIG. 3, is used in many implantable stimulators (10) to conserve space.

Figure 4:
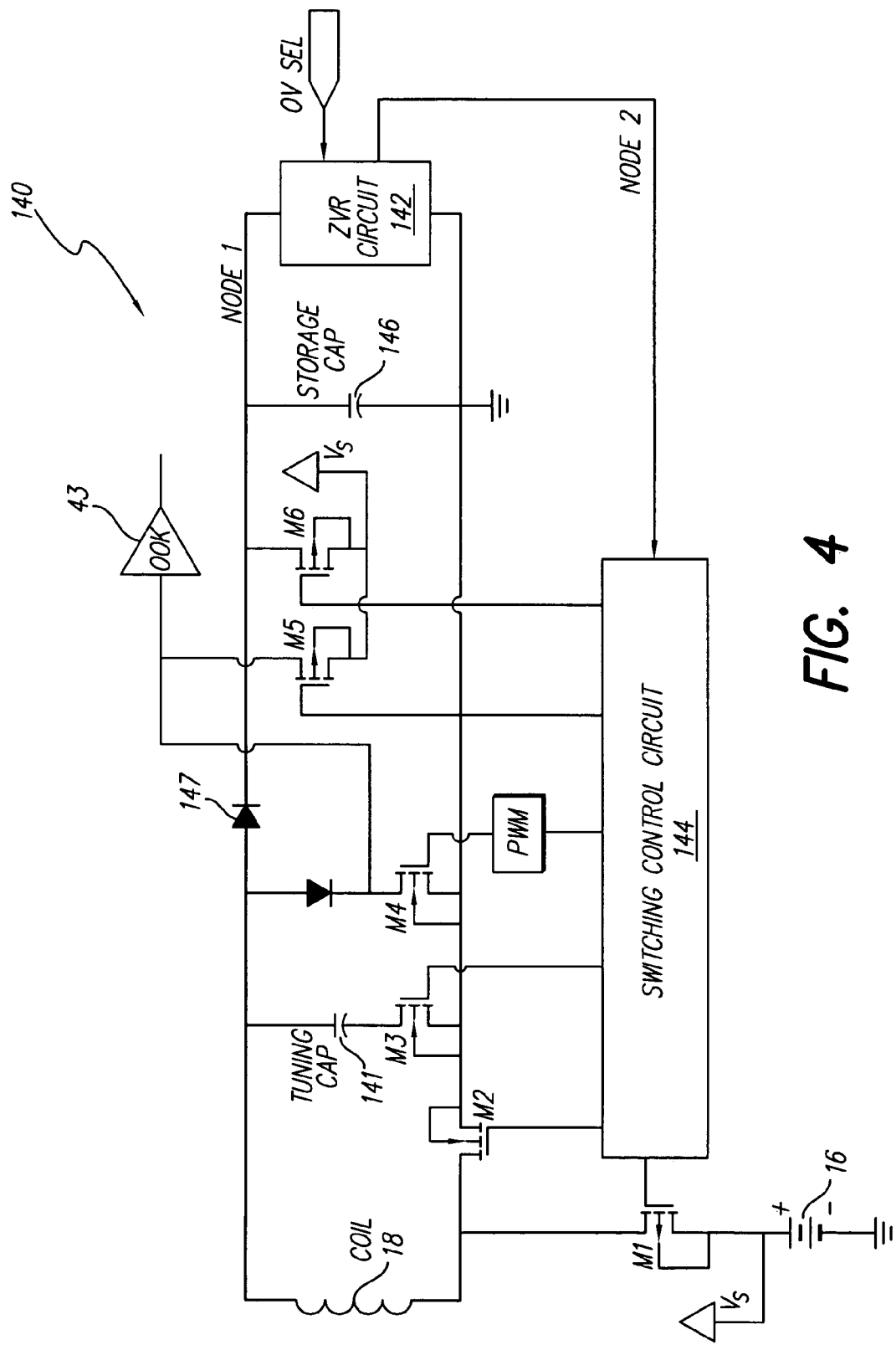
FIG. 4 shows a front end circuit that may be used in connection with a multiplexed coil to control the mode of operation of the stimulator according to principles described herein.

FIG. 4 shows a front end circuit (140) that may be used in connection with the multiplexed coil (18) to control the mode of operation of the stimulator (10). As shown in FIG. 4, the front end circuit (140) includes a number of transistor switches M1-M6. The transistor switches M1-M6 in FIG. 4 are CMOS transistors for illustrative purposes only and may be any type of transistor or other electronic switch. Six transistor switches are shown in FIG. 4 for illustrative purposes only. It will be recognized that any number of transistor switches may be included in the front end circuit (140) as best serves a particular application. Each transistor switch M1-M6 is controlled by a switching control circuit (144). The switching control circuit (144) may be a digital CMOS circuit such as a state machine, for example, or any other circuit (144) configured to control the transistor switches M1-M6.

Figure 6:
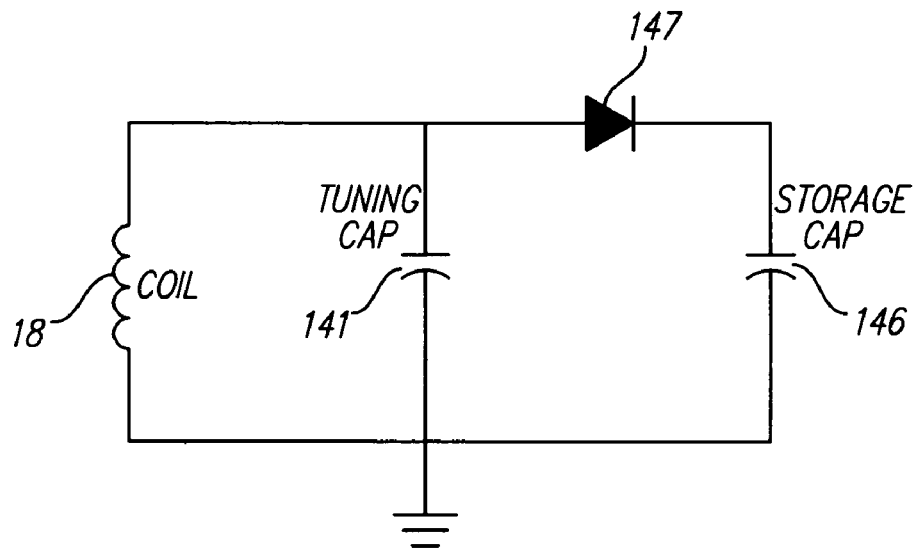
FIG. 6 illustrates a charging circuit used in a charging mode according to principles described herein.

Each of the transistor switches M1-M6 may operate in an ON or OFF state. The state of each the transistor switches determines the mode of operation of the stimulator (10). FIG. 5 is a table that lists the states of the transistor switches M1-M6 for a number of modes of operation of the stimulator (10). As shown in FIG. 5, in order for the stimulator (10) to operate in a charging mode, M1 is turned OFF, M2 is turned ON, M3 is turned ON, M4 is turned OFF, M5 is turned OFF, and M6 is turned ON. In the charging mode, the front end circuit (140) of FIG. 4 effectively becomes a charging circuit, as shown in FIG. 6. The charging circuit, as shown in FIG. 6, includes a tuning capacitor (141) connected in parallel with the coil (18). The coil (18) and the tuning capacitor (141) comprise an "LC" circuit that is tuned to the frequency of an incoming RF signal. The charging circuit may further include a diode (147) configured to rectify the received RF signal and a storage capacitor (146) configured to store the rectified RF signal. The rectified signal may then be used to charge the battery (16; FIG. 3).

Figure 7:
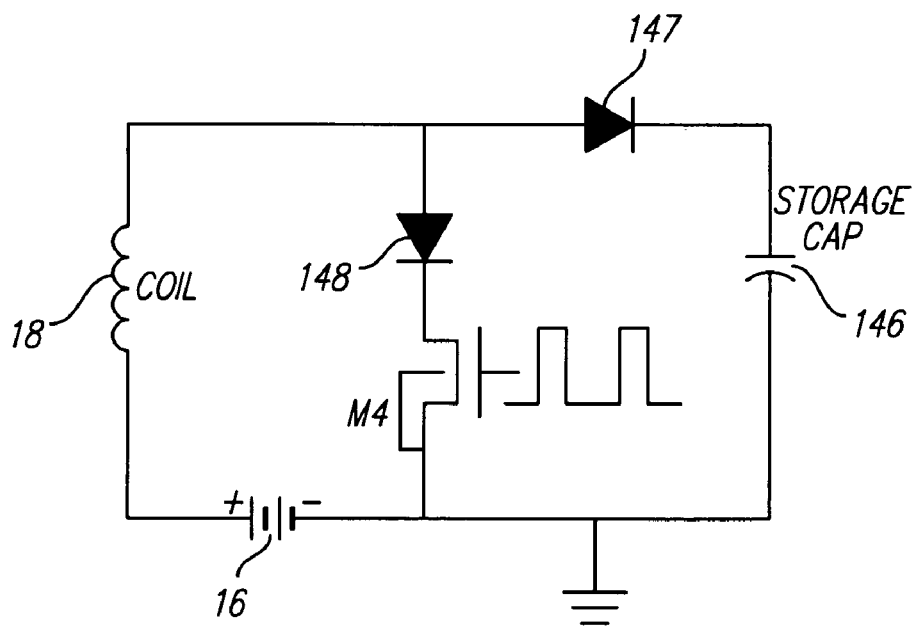
FIG. 7 illustrates a step-up circuit used in a step-up mode according to principles described herein.

Similarly, as shown in FIG. 5, the stimulator (10) may operate in a step-up mode if M1 is turned ON, M2 and M3 are turned OFF, M4 is modulated (SWITCH) with a pulse width modulation (PWM) signal by a PWM circuit (145; FIG. 4), and M5 and M6 are turned OFF. In the step-up mode, the front end circuit (140) of FIG. 4 effectively becomes a step-up circuit, as shown in FIG. 7. The step-up circuit, as shown in FIG. 7, may include the diode (147), an additional diode (148), the transistor switch M4, and the storage capacitor (146). The transistor switch M4 outputs a stepped-up output voltage that may be used by the pulse generator (52; FIG. 3) or by any other component within the implantable stimulator (10; FIG. 3).

Figure 8:
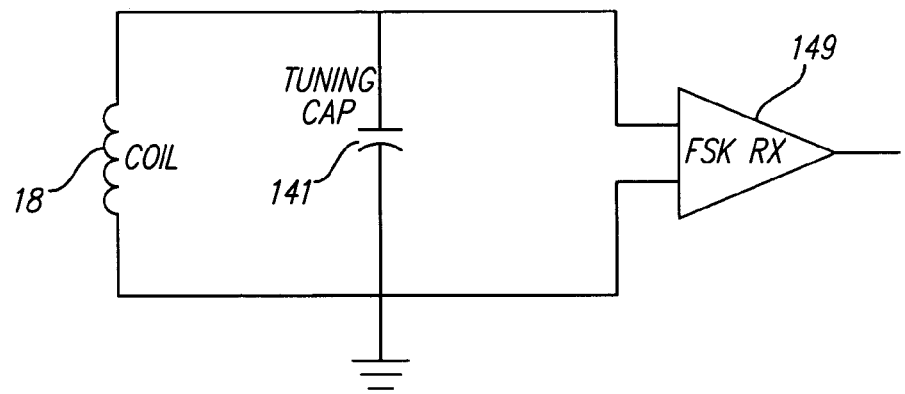
FIG. 8 illustrates a frequency shift keying receiving (FSK RX) circuit used in an FSK RX mode according to principles described herein.

Referring again to FIG. 5, the stimulator (10) may operate in an FSK receiving (FSK RX) mode if M1 is turned OFF, M2 and M3 are turned ON, M4 is turned OFF, and M5 and M6 are turned ON. In the FSK RX mode, the front end circuit (140) of FIG. 4 effectively becomes an FSK RX circuit, as shown in FIG. 8. The FSK RX circuit, as shown in FIG. 8, may include the coil (18), the tuning capacitor (141), and an FSK receiver (FSK RX) (149). The FSK receiver (149) may be the receiver (42) of FIG. 3 or it may be a separate receiver. The FSK RX circuit tunes the coil (18) to the same frequency used by the external device (20; FIG. 1) or by any other device with which the stimulator (10) is communicating. The frequency used by the external device (20; FIG. 1) may be any frequency as best serves a particular application. For example, the frequency may be substantially equal to 127 kHz in some applications.

Figure 9:
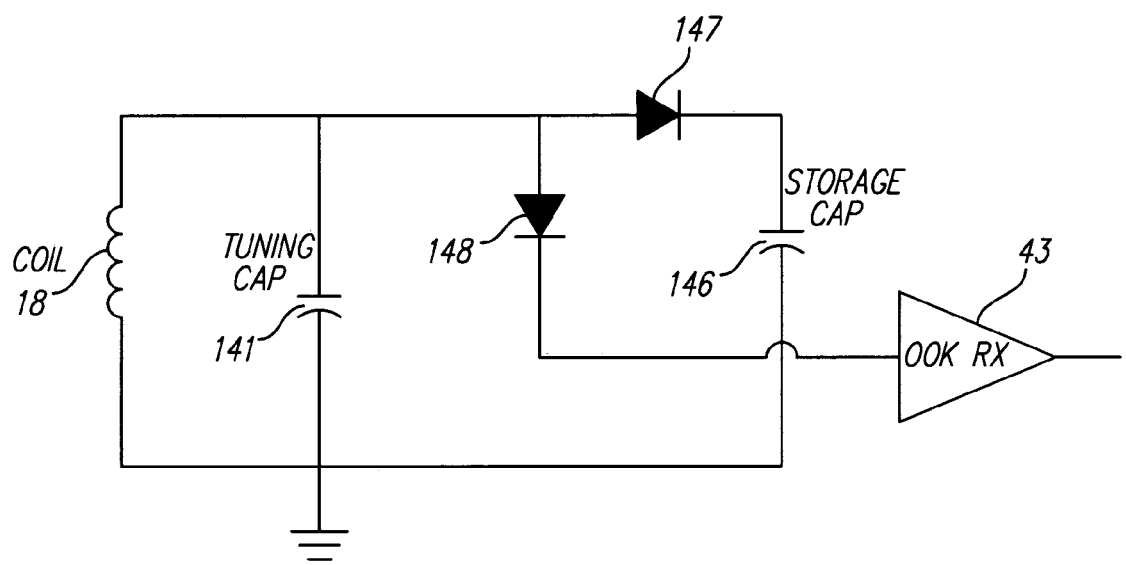
FIG. 9 illustrates an on-off keying receiving (OOK RX) circuit used in an OOK RX mode according to principles described herein.

FIG. 5 also shows that the stimulator (10) may operate in an OOK receiving (OOK RX) mode if M1 is turned OFF, M2 and M3 are turned ON, and M4-M6 are turned OFF. In the OOK RX mode, the front end circuit (140) of FIG. 4 effectively becomes an OOK RX circuit, as shown in FIG. 9. The OOK RX circuit, as shown in FIG. 9, may include the coil (18), the tuning capacitor (141), the diodes (147, 148), the storage capacitor (146), and the OOK receiver (OOK RX) (43).

Figure 10:
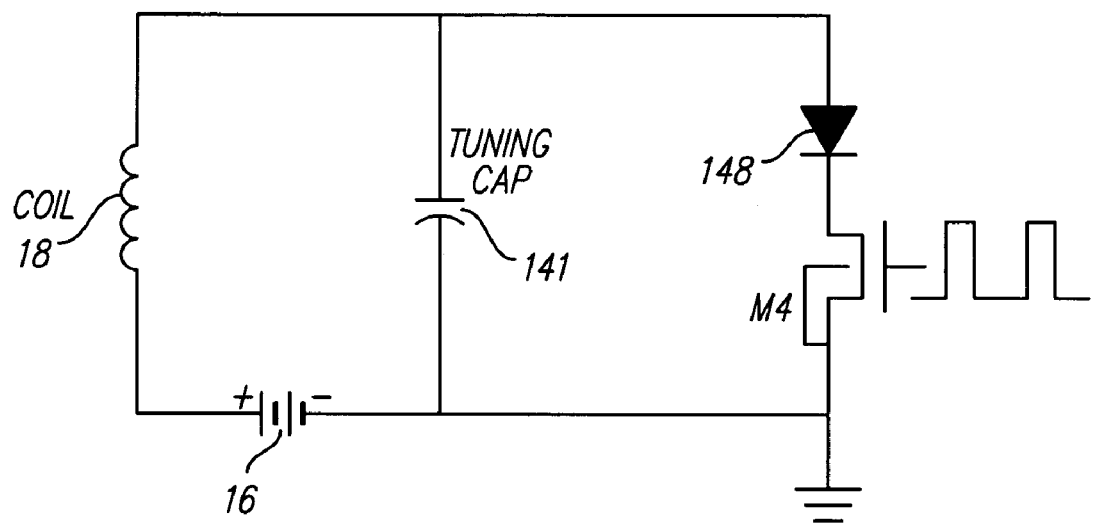
FIG. 10 illustrates a transmitting circuit used in a transmitting mode according to principles described herein.

FIG. 5 also shows that the stimulator (10) may operate in a transmitting mode if M1 is turned ON, M2 is turned OFF, M3 is turned ON, M4 is modulated (SWITCH) with a PWM signal by the PWM circuit (145; FIG. 4), and M5 and M6 are turned OFF. In the transmitting mode, the front end circuit (140) of FIG. 4 effectively becomes a transmitting circuit, as shown in FIG. 10. The transmitting circuit, as shown in FIG. 10, may include the coil (18), the tuning capacitor (141), the diode (148), the transistor switch M4, and the battery (16).

Hence, as shown in FIGS. 6-10, the components of FIG. 4 may be used in a variety of different configurations depending on the states of the transistor switches M1-M6. However, if all the gates of the switches M1-M6 are at zero volts, (i.e., the battery (16) is depleted to a level substantially equal to zero volts), the coil (18) cannot be tuned to the frequency of an incoming RF signal and therefore cannot be charged. In particular, if the transistor switches M2 and M3 are not turned ON, the stimulator (10) cannot operate in the charging mode. Thus, as shown in FIG. 4, the front end circuit (140) also includes a zero volt recovery (ZVR) circuit (142). The ZVR circuit (142) is configured to receive recovery power transmitted by the booster coil (411; FIG. 1) and use the recovery power to control one or more of the transistor switches M1-M6. In particular, the ZVR circuit (142) receives a burst of energy in a frequency range near a self-resonance frequency of the coil (18) and uses the energy to power one or more of the transistor switches M1-M6 such that the coil (18) may again be tuned to the transmitting frequency of the antenna/charging coil (34; FIG. 1) of the external device (20; FIG. 1). The self-resonance frequency of the coil (18) is the natural resonant frequency of the coil (18), i.e., the frequency at which the coil (18) may receive an incoming RF signal when not tuned to a particular tuning frequency by the tuning capacitor (141; FIG. 4) or by any other tuning circuitry.

Figure 11:
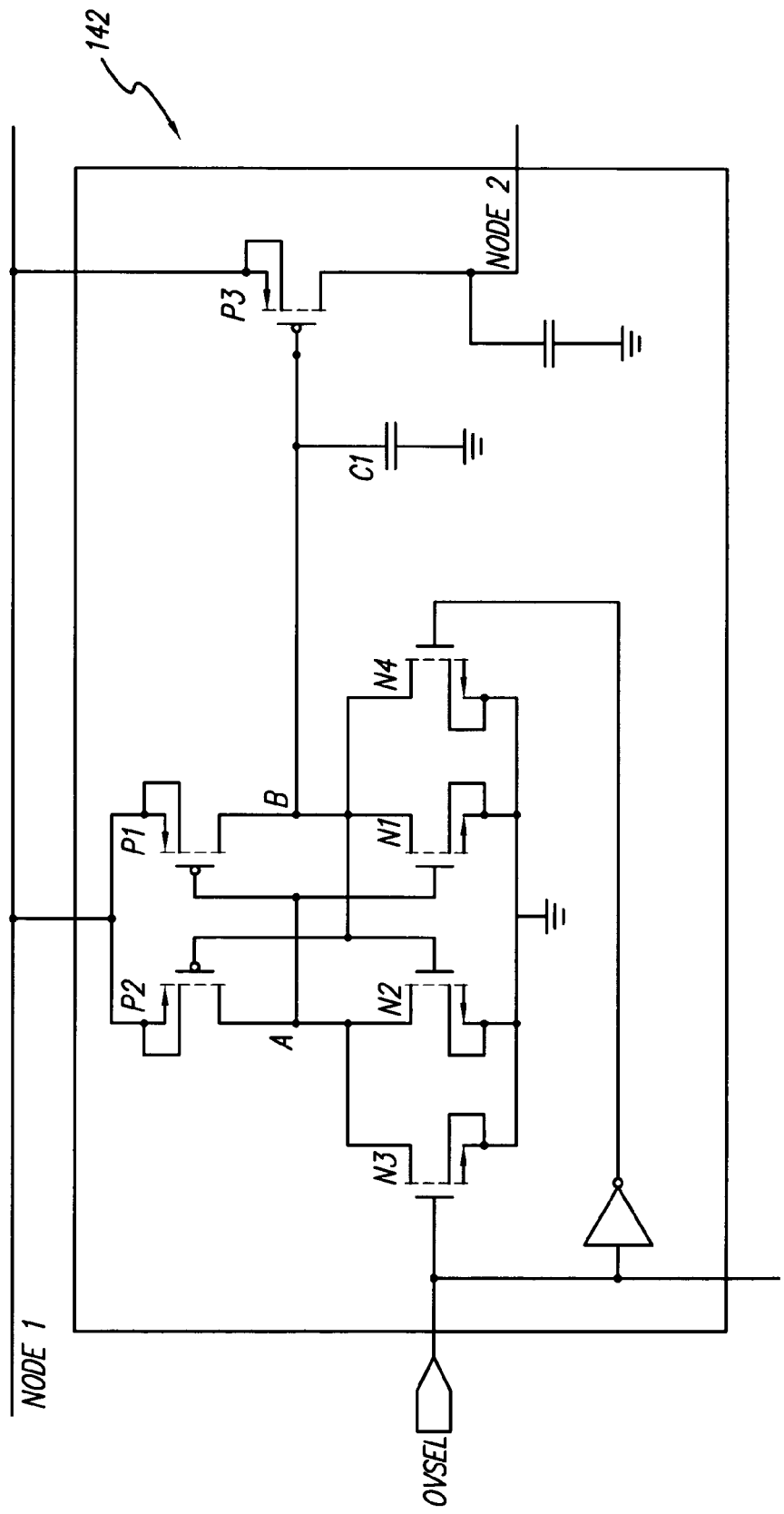
FIG. 11 is a diagram of an exemplary zero volt recovery (ZVR) circuit according to principles described herein.

FIG. 11 is a diagram of an exemplary ZVR circuit (142). The ZVR circuit (142) may include additional circuitry to the circuitry shown in FIG. 11. Examples of such additional circuitry will be described in more detail below. As shown in FIG. 11, the ZVR circuit (142) includes a number of transistor switches (P1-P3 and N1-N4) and a capacitor C1. The transistor switches P1-P2 and N1-N4 are arranged in an asymmetric static random access memory (SRAM) cell configuration. Hence, as will be recognized by one of skill in the art, if N3 is ON, then N4 is OFF, N2 is ON, P1 is ON, P2 is OFF, and N1 is OFF. The asymmetric SRAM cell allows the ZVR circuit (142) to provide recovery power for the transistor switches M1-M6 in FIG. 4 while consuming little or no current. Furthermore, the asymmetric SRAM cell may have a programmable power-up value that allows the ZVR circuit (142) to deterministically configure the transistor switches M1-M6 immediately after receiving power from the boost field. Hence, the asymmetric SRAM cell has little or no quiescent power consumption.

As shown in FIG. 11, the ZVR circuit (142) is enabled by a select signal (0VSEL). The select signal may be HIGH or LOW. For illustrative purposes only, the ZVR circuit (142) is enabled when the select signal is LOW. Hence, if the battery (16; FIG. 4) is not in a zero volt state, the select signal is HIGH. A HIGH select signal turns a transistor switch N3 ON. If N3 is ON, P1 is ON and the voltage at node B is equal to the voltage at node 1. Node 1 is the input node of the ZVR circuit (142). Hence, the transistor switch P3 is OFF and the voltage at node 2, the output node of the ZVR circuit (142), is equal to $V_S$, the voltage output by the battery (16; FIG. 4). With node 2 equal to $V_S$, the switching control circuitry (144) of FIG. 4 is powered by the battery (16; FIG. 4).

However, if the battery (16; FIG. 4) is in a zero volt state, the select signal (0VSEL) is LOW and the ZVR circuit (142) is enabled. In other words, P3 is ON, making the voltage at node 2 equal to the voltage at node 1. With node 2 equal to node 1, the ZVR circuit (142) is configured to process the boost field emitted by the booster coil (411; FIG. 1) and received by the coil (18; FIG. 1). As mentioned, the boost field is sent to the coil (18; FIG. 1) at a frequency near the self-resonance frequency of the coil (18; FIG. 1). The boost field frequency may be any frequency as best serves a particular application. For example, the boost field frequency may be substantially equal to 1.5 MHz. The self-resonance frequency may be affected in part by the parasitic capacitance of the various components in the stimulator (10; FIG. 1). The boost field may have a duration of a few milliseconds or for any other time period as best serves a particular application.

Returning to FIG. 11, the application of the boost field to the enabled ZVR circuit (142) causes the voltage at node 1 (and therefore node 2) to increase. The increase in voltage at node 2 may then cause an increase in voltage at the gates of one of more of the transistor switches M1-M6 in FIG. 4. In some embodiments, the increase in voltage at node 2 causes a HIGH signal to be applied to the gates of the transistor switches M1-M3 in FIG. 4. Thus, M1 will be turned OFF and M2 and M3 will be turned ON. With M2 and M3 both ON, the front end circuit (140; FIG. 4) may tune the coil (18) to the frequency of the antenna/charging coil (34; FIG. 1) and the stimulator (10; FIG. 1) may begin to receive charging power via the bidirectional telemetry link (48; FIG. 1).

Figures 1, 12:
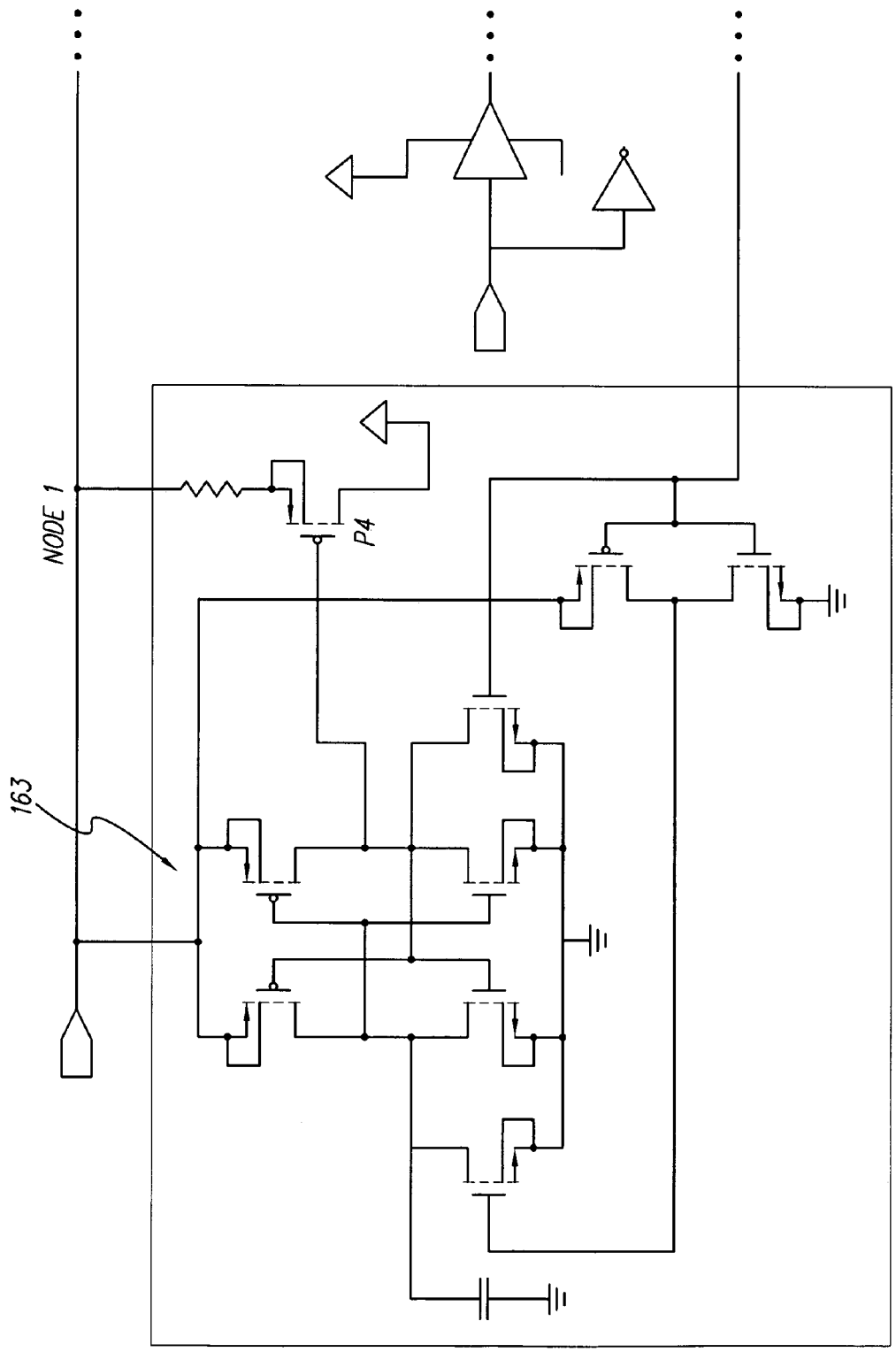
FIG. 12 illustrates additional circuitry in the ZVR circuit configured to trickle charge the battery, provide over voltage protection, provide trigger detection, and output gate voltage generation for one or more of the transistor switches M1-M6 according to principles described herein.
Figures 2, 12:
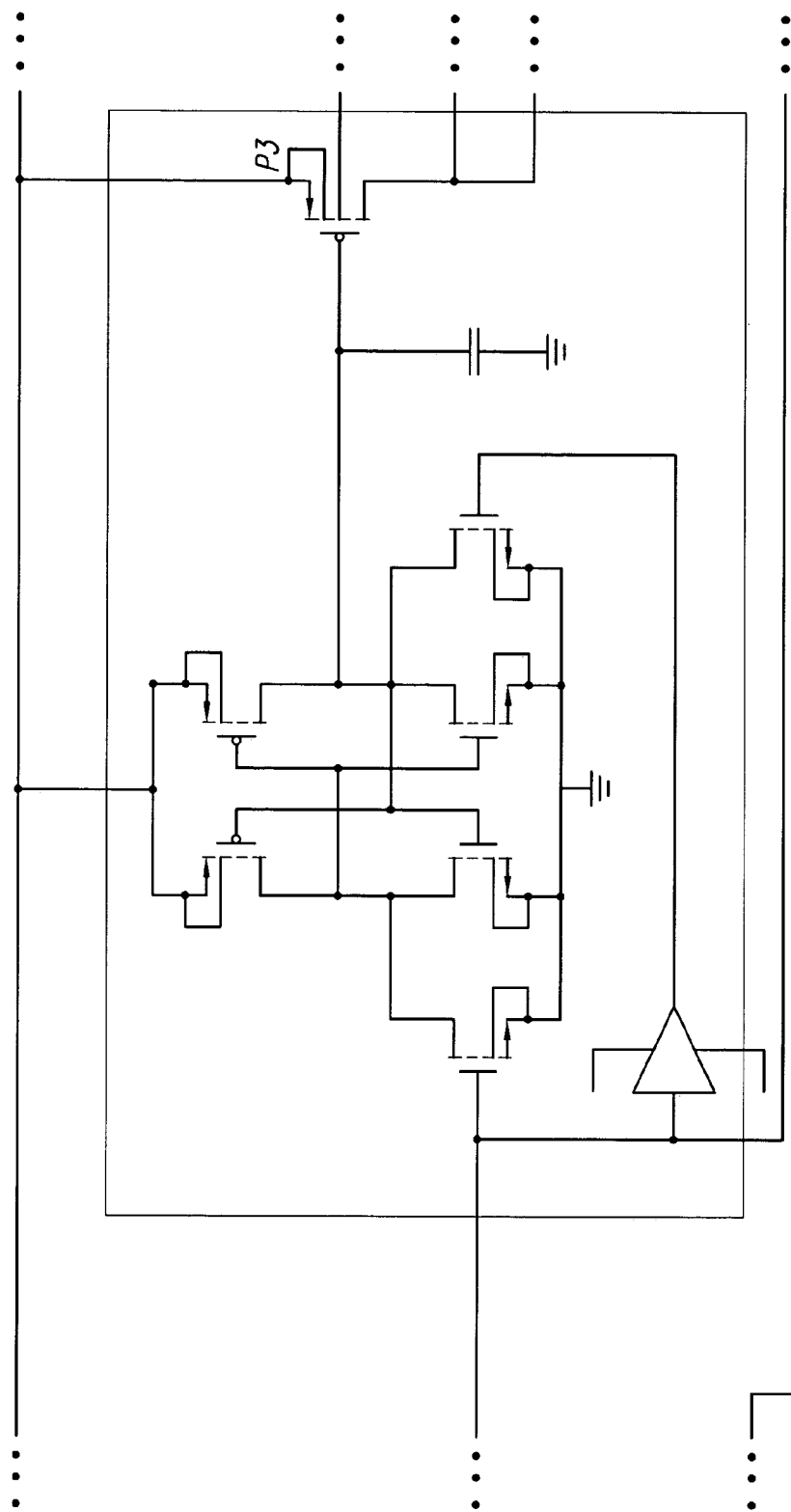
Figures 3, 12:
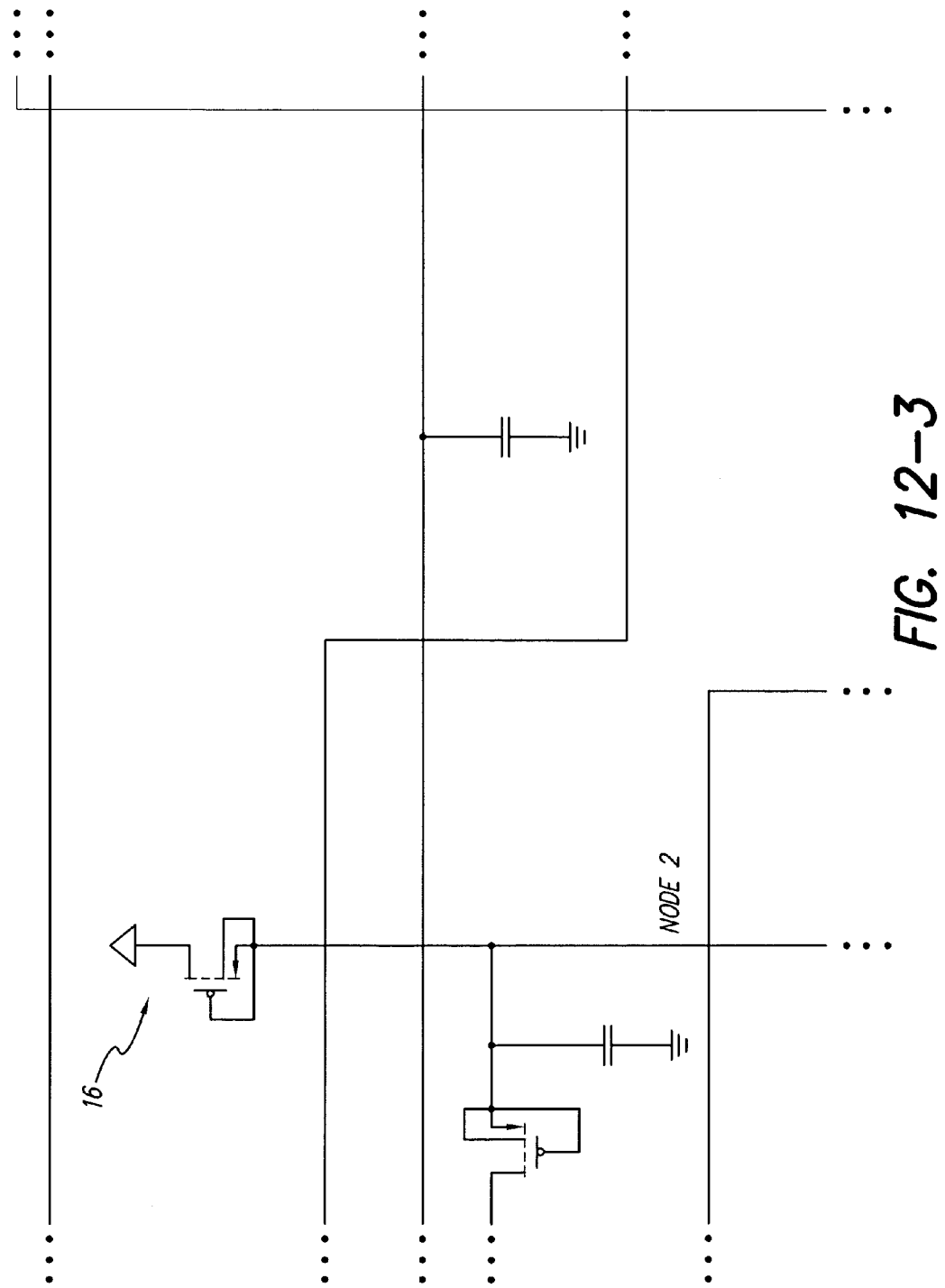
Figures 4, 12:
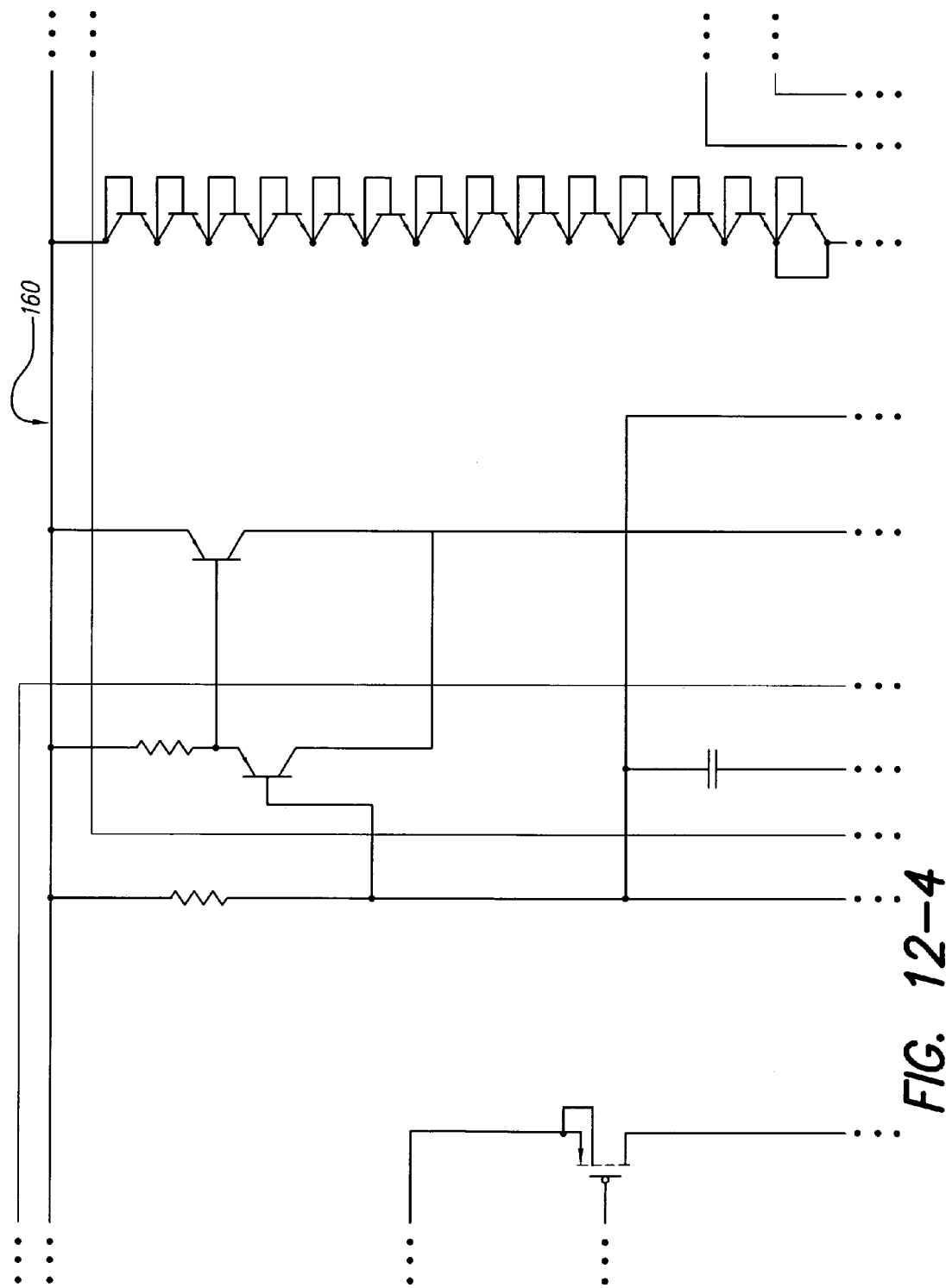
Figures 6, 12:
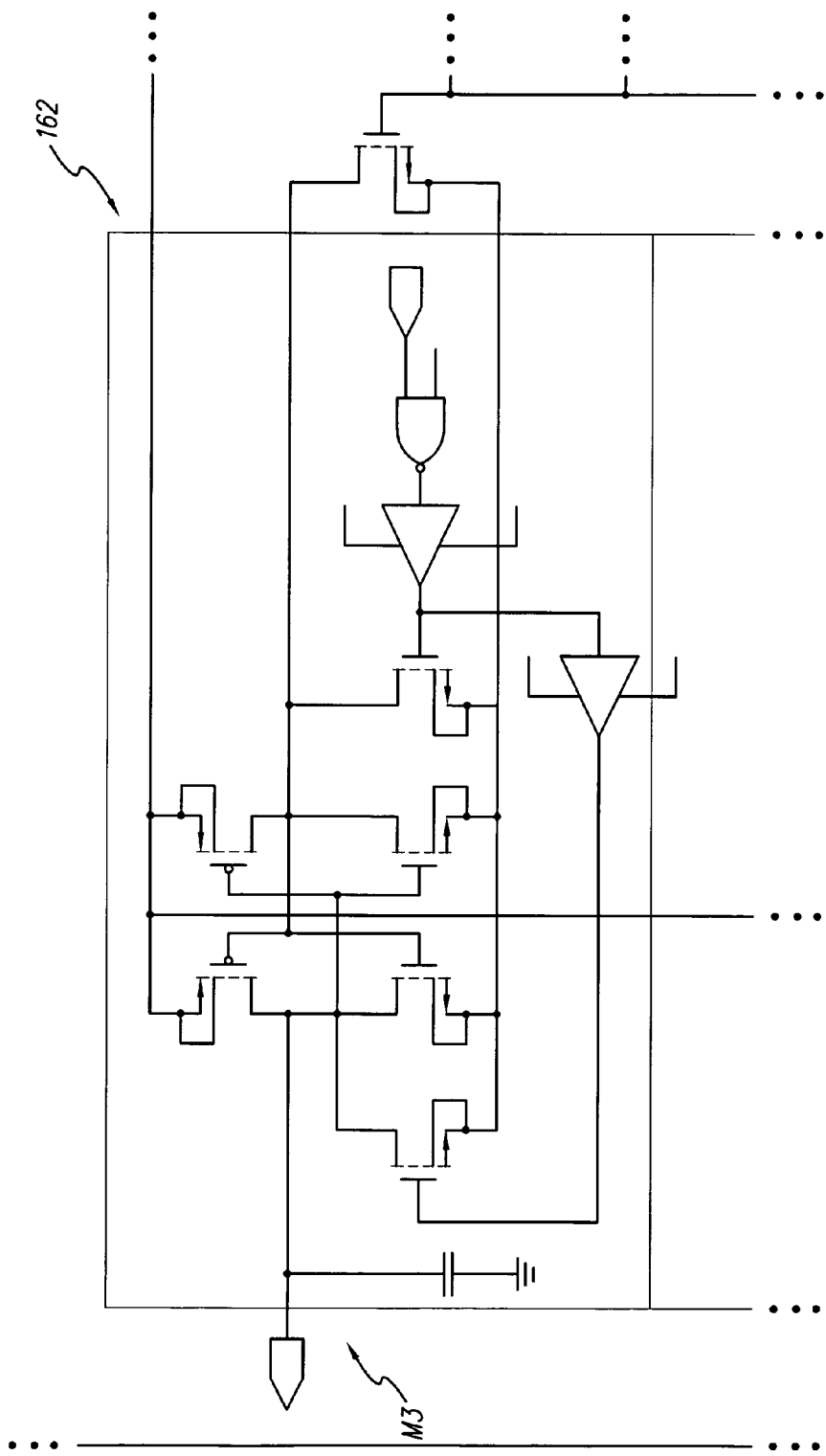
Figures 7, 12:
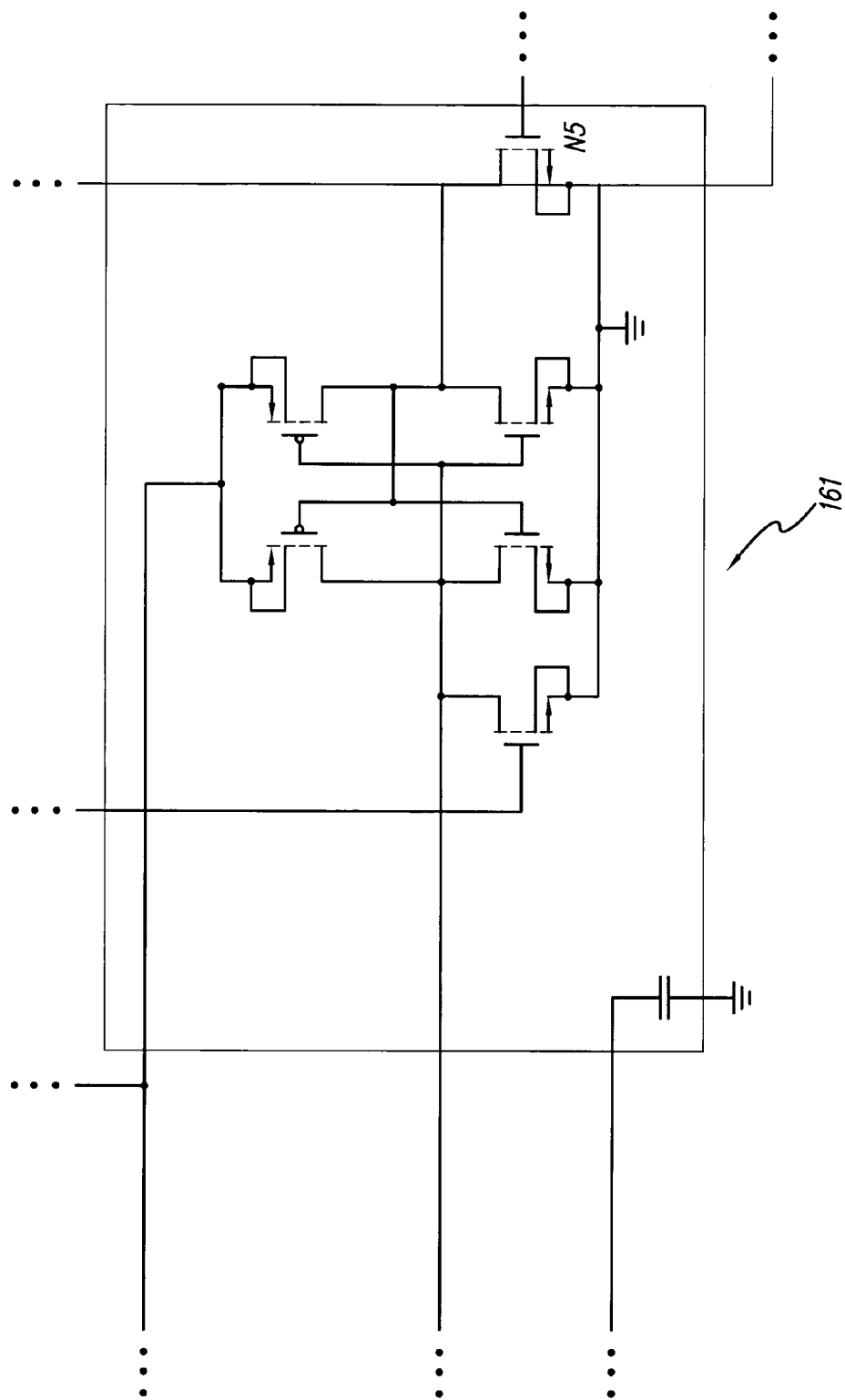
Figures 8, 12:
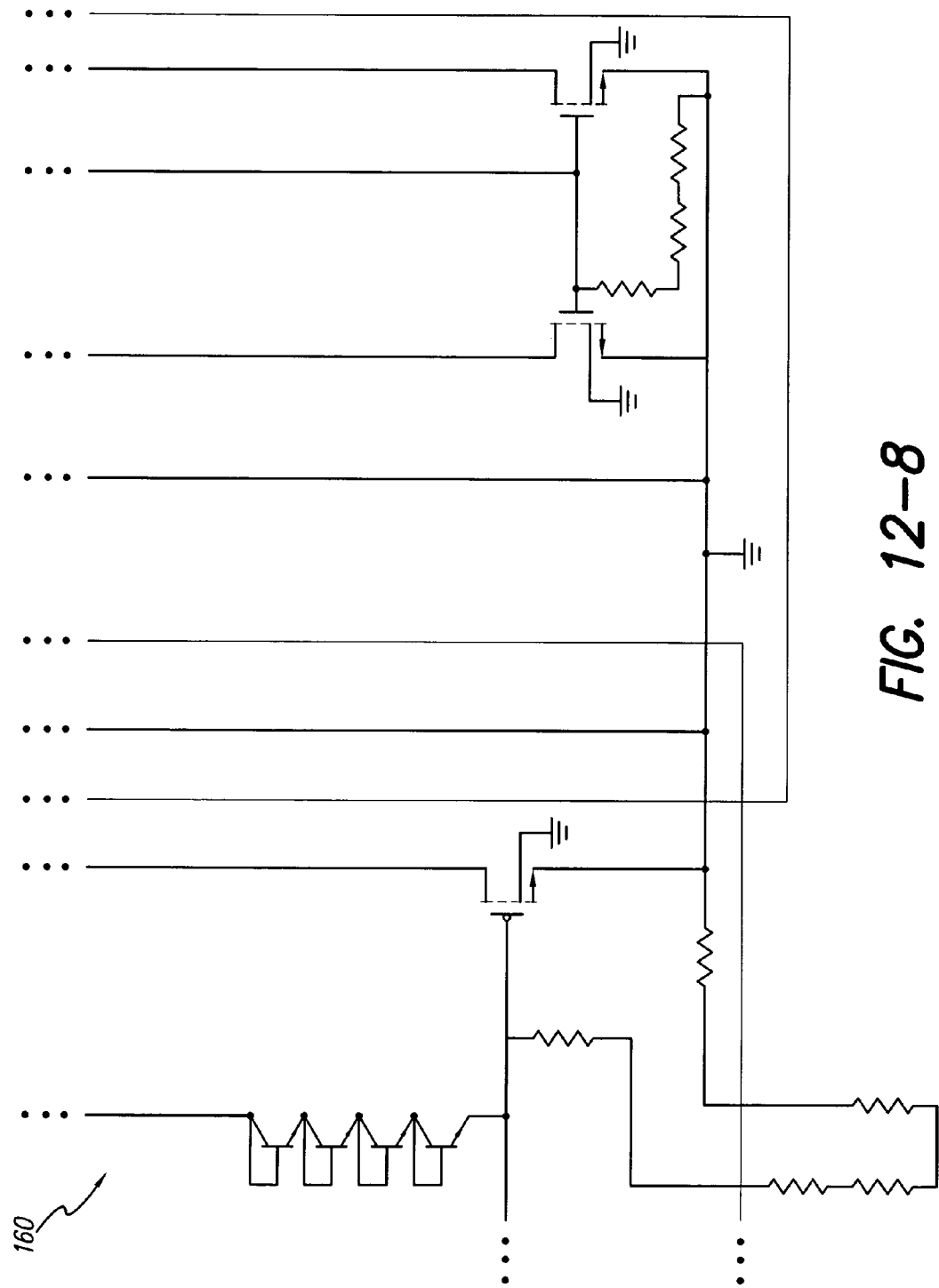
Figures 9, 12:
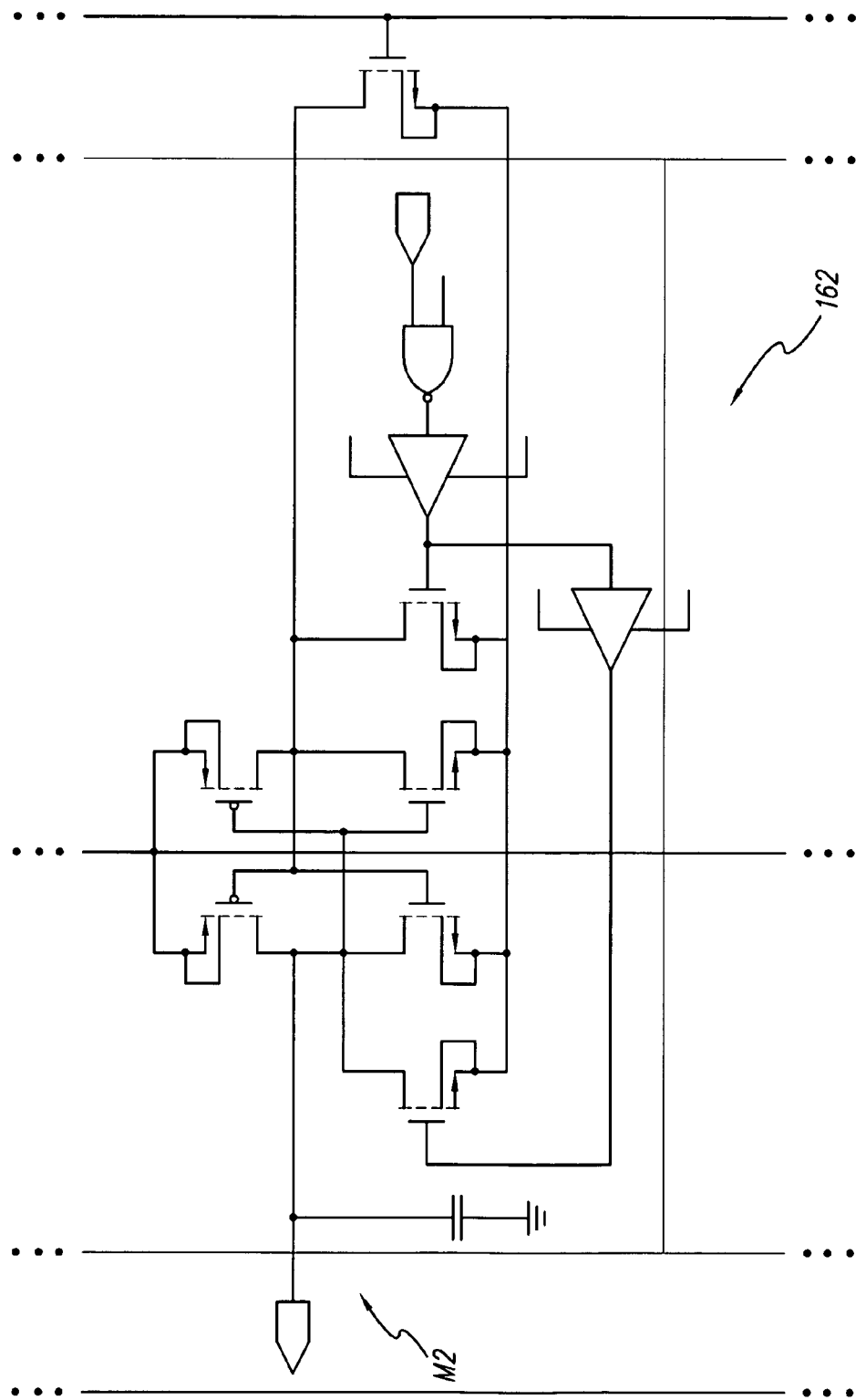
Figures 10, 12:
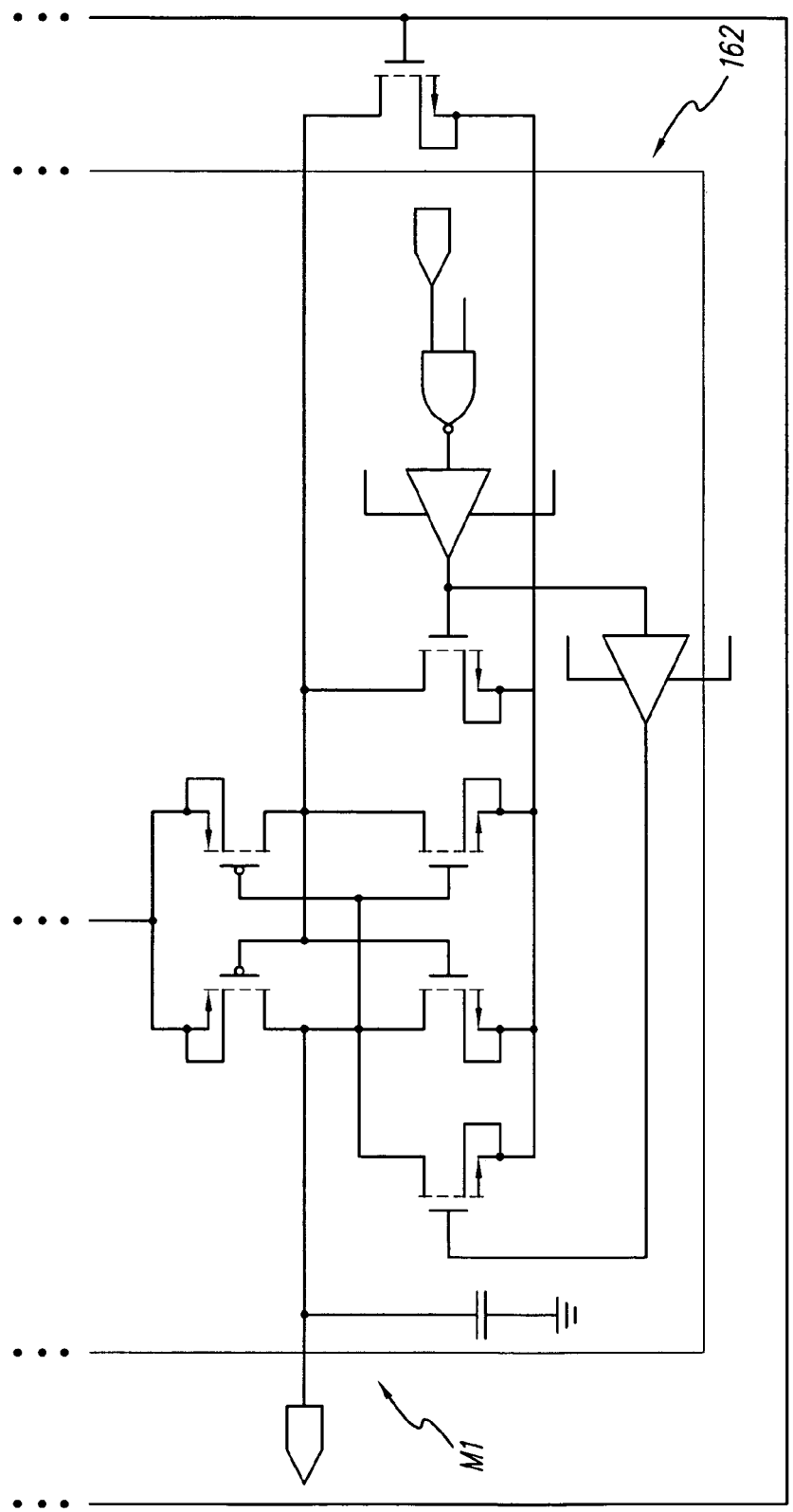

FIG. 12 shows that the ZVR circuit (142) of FIG. 11 may also include, but is not limited to, a trickle charge circuit (163) configured to trickle charge the battery (16), an over voltage protection circuit (160) configured to provide over voltage protection, a trigger detection circuit (161) configured to provide trigger detection, and/or an output gate voltage generation circuit (162) configured to provide output gate voltage for one or more of the transistor switches M1-M6 in FIG. 4. As shown in FIG. 12, the trigger detection circuit (161), the trickle charge circuit (163) and the output gate voltage generation circuit (162) may include one or more asymmetric SRAM cells.

The over voltage protection circuit (160) of FIG. 12 may be configured to provide over voltage protection during zero volt recovery and/or during normal operation of the stimulator (10; FIG. 3). For example, as shown in FIG. 12, the over voltage protection circuit (160) may provide 5.5 volt protection during zero volt recovery and 9 volt protection during normal operation of the stimulator (10; FIG. 3). Over voltage protection of 5.5 volts and 9 volts are merely illustrative levels of over volt protection. The over voltage protection circuit (160) may provide any level of over voltage protection. The over volt protection circuit (160) may also act as a digital buffer of the switch gate voltages for transistor switches M1-M6.

The trickle charge circuit (163) of FIG. 12 is configured to trickle charge the battery (16) through transistor switch P4 as long as transistor switch N5 in the over voltage protection circuit (160) is ON. The trigger detector circuit (161) may be configured to detect a change in the voltage on node 2 such that the asymmetric SRAM cells in the output gate voltage generation circuit (162) may flip and output a HIGH signal for the gate voltages of M1-M3.

Figure 13:
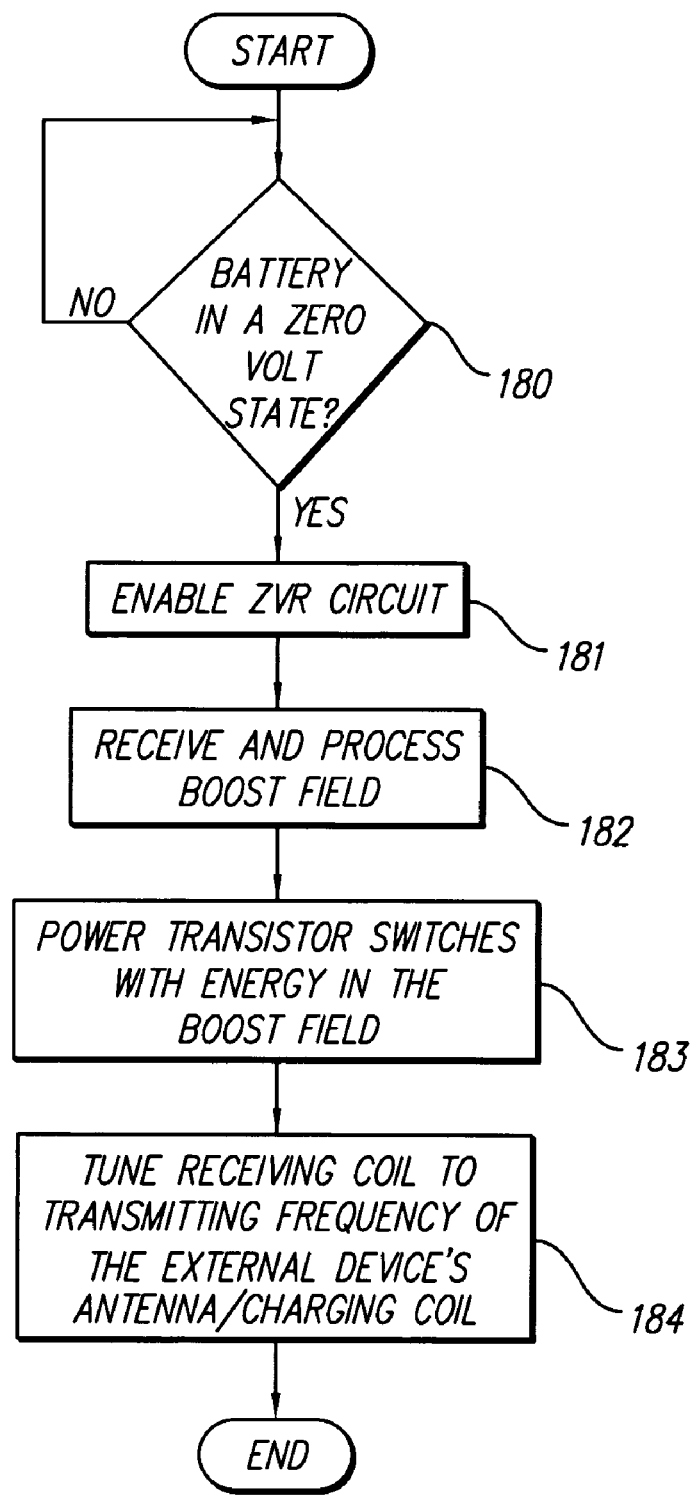
FIG. 13 is a flow chart illustrating an exemplary method of performing zero volt recovery for a battery in an implantable stimulator that is in a zero volt state according to principles described herein.

FIG. 13 is a flow chart illustrating an exemplary method of performing zero volt recovery for a battery (16; FIG. 4) in an implantable stimulator (10; FIG. 4) that is in a zero volt state. It is first determined whether the battery (16; FIG. 4) is in a zero volt state (step 180). If the battery (16; FIG. 4) is in a zero volt state (Yes; step 180), the ZVR circuit (142; FIG. 4) is enabled (step 181). Once the ZVR circuit (142; FIG. 4) has been enabled (step 181), a boost field emitted by the booster coil (411; FIG. 1) may be received and processed (step 182). The energy in the boost field may then be used to power one or more of the transistor switches M1-M6 in FIG. 4 (step 183). Once one or more of the transistor switches M1-M6 have been turned ON, the coil (18; FIG. 4) may be tuned to the transmitting frequency of the antenna/charging coil (34; FIG. 1) of the external device (20; FIG. 1).

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A system for providing power to a rechargeable battery in an implantable stimulator, said system comprising:
a first coil configured to emit a first magnetic field;
a second coil in said stimulator configured to receive said first magnetic field; and
a zero volt recovery (ZVR) circuit in said stimulator configured to use said first magnetic field to cause said second coil in said stimulator to be tuned to a frequency of a second magnetic field, said second magnetic field used to provide said power to said battery.

2. The system of claim 1, wherein said first magnetic field has a frequency substantially equal to a self-resonance frequency of said second coil in said simulator.

3. The system of claim 1, wherein said frequency of said first magnetic field is substantially equal to 1.5 megahertz.

4. The system of claim 1, wherein said stimulator comprises a front end circuit having a number of transistor switches, each of said transistor switches being in an ON state or an OFF state, wherein said states of said transistor switches select a mode of operation of said stimulator out of a number of modes of operation, said number of modes of operation including a charging mode wherein said battery is charged with said second magnetic field.

5. The system of claim 4, wherein said number of modes of operation further includes a step-up mode, a frequency shift keying (FSK) receiving mode, an on-off keying(OOK) receiving mode, and a transmitting mode.

6. The system of claim 4, wherein said ZVR circuit comprises an over voltage protection circuit configured to provide over voltage protection during any of said number of modes of operation.

7. The system of claim 4, wherein said ZVR circuit uses said first magnetic field to turn ON one or more of said transistor switches such that said mode of operation of said stimulator is said charging mode.

8. The system of claim 7, wherein said ZVR circuit uses said first magnetic field to turn OFF one or more of said transistor switches such that said mode of operation of said stimulator is said charging mode.

9. The system of claim 7, wherein said ZVR circuit comprises an output gate voltage generation circuit configured to generate a voltage used to turn said one or more of said transistor switches to said ON state.

10. The system of claim 1, wherein said ZVR circuit comprises a trickle charge circuit configured to trickle charge said battery.

11. The system of claim 1, wherein said ZVR circuit comprises one or more asymmetric static random access memory (SRAM) cells.

12. The system of claim 1, wherein said frequency of said second magnetic field is substantially equal to 127 kilohertz.

13. The system of claim 1, wherein said system further comprises a third coil, said third coil configured to emit said second magnetic field.

14. An implantable stimulator, comprising:
a rechargeable battery;
a coil configured to receive a first magnetic field; and
a zero volt recovery (ZVR) circuit configured to use said first magnetic field to cause said coil to be tuned to a frequency of a second magnetic field, said second magnetic field used to provide power to said battery.

15. The stimulator of claim 14, wherein said first magnetic field has a frequency substantially equal to a self-resonance frequency of said coil.

16. The stimulator of claim 14, wherein said frequency of said first magnetic field is substantially equal to 1.5 megahertz.

17. The stimulator of claim 14, further comprising:
a front end circuit having a number of transistor switches, each of said transistor switches being in an ON state or an OFF state;
wherein said states of said transistor switches select a mode of operation of said stimulator out of a number of modes of operation, said number of modes of operation including a charging mode wherein said battery is charged with said second magnetic field.

18. The stimulator of claim 17, wherein said number of modes of operation further includes a step-up mode, a frequency shift keying (FSK) receiving mode, an on-off keying (OOK) receiving mode, and a transmitting mode.

19. The stimulator of claim 17, wherein said ZVR circuit comprises an over voltage protection circuit configured to provide over voltage protection during any of said number of modes of operation.

20. The stimulator of claim 17, wherein said ZVR circuit uses said first magnetic field to turn ON one or more of said transistor switches such that said mode of operation of said stimulator is said charging mode.

21. The stimulator of claim 20, wherein said ZVR circuit uses said first magnetic field to turn OFF one or more of said transistor switches such that said mode of operation of said stimulator is said charging mode.

22. The stimulator of claim 20, wherein said ZVR circuit comprises an output gate voltage generation circuit configured to generate a voltage used to turn said one or more of said transistor switches to said ON state.

23. The stimulator of claim 14, wherein said ZVR circuit comprises a trickle charge circuit configured to trickle charge said battery.

24. The stimulator of claim 14, wherein said ZVR circuit comprises one or more asymmetric static random access memory (SRAM) cells.

25. The stimulator of claim 14, wherein said frequency of said second magnetic field is substantially equal to 127 kilohertz.

26. A device configured to provide power to a rechargeable battery in an implantable stimulator, said device comprising:
a first coil configured to emit a first magnetic field of a first frequency used by a zero volt recovery (ZVR) circuit in said stimulator to cause a stimulator coil in said stimulator to be tuned to a frequency of a second magnetic field of a second frequency, said second magnetic field configured to provide said power to said battery; and
a second coil configured to emit said second magnetic field.

27. The device of claim 26, wherein said first frequency is substantially equal to a self-resonance frequency of said stimulator coil in said simulator.

28. The device of claim 26, wherein said first frequency is substantially equal to 1.5 megahertz.

29. The device of claim 26, further comprising control circuitry to activate the first coil before the second coil.

30. The device of claim 26, wherein said second frequency is substantially equal to 127 kilohertz.

31. A method of providing power to a rechargeable battery in an implantable stimulator, said method comprising:
transmitting a first magnetic field used to provide said power to said battery;
transmitting a second magnetic field; and
using said second magnetic field to cause a coil in said stimulator to be tuned to a frequency of said first magnetic field.

32. The method of claim 31, wherein said second magnetic field has a frequency substantially equal to a self-resonance frequency of said coil in said simulator.

33. The method of claim 31, wherein said frequency of said second magnetic field is substantially equal to 1.5 megahertz.

34. The method of claim 31, wherein said step of using said second magnetic field to cause said coil in said stimulator to be tuned to said frequency of said first magnetic field comprises controlling a state of a number of transistor switches with said second magnetic field.

35. The method of claim 31, further comprising trickle charging said battery.

36. The method of claim 31, wherein said frequency of said first magnetic field is substantially equal to 127 kilohertz.

37. A system for providing power to a rechargeable battery in an implantable stimulator, said system comprising:
means for transmitting a first magnetic field used to provide said power to said battery;
means for transmitting a second magnetic field; and
means for using said second magnetic field to cause a coil in said stimulator to be tuned to a frequency of said first magnetic field.

38. The system of claim 37, wherein said means for using said second magnetic field to cause said coil in said stimulator to be tuned to said frequency of said first magnetic field comprises means for controlling a state of a number of transistor switches with said second boost field.

* * * * *